United States Patent [19]

Oertle et al.

[11] Patent Number: 4,503,710

[45] Date of Patent: Mar. 12, 1985

[54] CRACK DETECTION BY ELECTRICAL RESISTANCE

[75] Inventors: Donald H. Oertle; Randall G. Ivie, both of Ponca City, Okla.

[73] Assignee: Conoco Inc., Ponca City, Okla.

[21] Appl. No.: 502,037

[22] Filed: Jun. 8, 1983

[51] Int. Cl.$^3$ ............................................. G01N 19/08
[52] U.S. Cl. ..................................... 73/763; 73/772; 73/786; 73/799
[58] Field of Search ................. 73/786, 787, 763, 768, 73/77 L, 775, 799; 324/65 R, 65 P

[56] References Cited

U.S. PATENT DOCUMENTS

| | | | |
|---|---|---|---|
| 3,383,863 | 5/1968 | Berry | 324/65 P |
| 3,738,162 | 6/1973 | Dally et al. | 73/787 |
| 3,803,485 | 4/1974 | Crites et al. | 73/763 |
| 3,855,531 | 12/1974 | Fielibert et al. | 324/65 R |
| 4,346,591 | 8/1982 | Evans | 73/46 |
| 4,425,054 | 1/1984 | Blondy et al. | 73/40 |
| 4,448,080 | 5/1984 | Dressel et al. | 73/40 |

Primary Examiner—Anthony V. Ciarlante
Attorney, Agent, or Firm—Cortlan R. Schupbach

[57] ABSTRACT

Early detection of cracks in structural members subject to stress is accomplished before cracks traverse the member by (a) affixing multiple liquid impermeable enclosures to the material to be monitored such that a crack forming in the monitored material will provide passage for liquid to enter the enclosures either through the monitored materials or by destroying the integrity of said liquid impermeable enclosures;

(b) sealing a resistor having a known value onto each of the enclosures, each of the resistors having one lead capable of liquid contact within the enclosure, said lead electrically isolated from the material being monitored and/or a second wire in the enclosures;

(c) forming a circuit connecting the multiple enclosures wherein the opposite resistor leads in each enclosure are connected by insulated wire to means for measuring resistance and/or conductance wherein each resistor alone or together with any combination of other resistors in said enclosures within the circuit provides a unique total resistance and/or conductance value if the exposed lead becomes liquid wet, and (d) monitoring resistance and/or conductance of the circuit, such that a crack in a monitored material will destroy the integrity of the enclosure, allowing the liquid to enter the enclosure and complete the circuit, wherein the location of each fluid filled enclosure is determined by the unique resistance and/or conductance measured.

12 Claims, 8 Drawing Figures

CRACK DETECTION BY ELECTRICAL RESISTANCE

This invention relates to early detection of crack formation in structural members subject to stress. The application has particular relevance in the early detection of cracks in critical stress members of offshore platforms employed to drill for or produce oil or gas.

Crack formation in permeable and non-permeable members subject to stress is a problem long recognized and one which has received much attention in recent years. In one example, offshore producing and drilling platforms are an important aspect of fulfilling the energy needs of the nation and the world. Such platforms are being fabricated to drill and produce in deeper and deeper water. For example, structures are now being planned and constructed for waters 900 feet or more in depth. While such platforms remain in many instances, the most practical way of recovering hydrocarbons from such depths, the great depths and turbulent environmental conditions combined to push the technology of platform construction to approach the state of the art for metallurgy and designs involved. In another example, in an effort to conserve space and move larger amounts of natural gas, often such materials are liquified and placed in concrete containers which have cryogenic properties much superior to steel or metal containers. Such containers are being fabricated and located in many locations around the world. Many ships made of concrete have been made or designed to carry liquified natural gas (LNG) at very low cryogenic temperatures, the concrete cargo container being much superior to insulated steel at the temperatures encountered.

Further examples of structural materials subject to stress and critical to operation, safety and the like exist. Examples are weld joints joining hull plates on tankers and the like, in helicopter blades, aircraft members, highly stressed crane members, bridge members, reactor members, pressure vessels or the like. When such members fail due to stress cracking, the results can be catastropic loss of human life and equipment, as well as loss of productivity.

Therefore, it is extremely important that any crack forming on such structural members be detected at the earliest possible stage such that appropriate repair can be made or if immediate repairs are impossible, personnel be evacuated and operations closed down.

Various attempts have been made to detect such early cracks, the earliest of such methods being visual inspection. Such visual inspections are known and enhanced by applying a material to the member, removing the material from the surface and applying a second material to react with the first material to form a dye, so that any first material oozing from a crack causes the crack to stand out to visual inspection. Such methods, however, are sometimes not feasible, particularly in underwater applications.

Acoustic emission methods have been employed, but require relatively complex, expensive equipment which detect cracks only while the cracks are actually forming, and are not noticeably effective in non-permeable porous materials, since these tend to dampen sound and give misleading results. Metallic materials can also be checked using magnetic methods, but these methods are less effective when the materials are in contact with a fluid. This method is not practical for application to permeable or porous and non-magnetic materials.

Ultrasonic tests have been employed in the prior art, but are surface geometry dependent and require smooth surfaces without voids in order to give an accurate reading. In addition, these tests are dampened by materials in contact with fluids and porous or permeable materials are not effectively protected or monitored by such methods.

U.S. Pat. Nos. 4,145,915 and 4,135,386 teach methods of detecting early crack formation by welding or attaching solid plates over the area to be monitored, then applying a pressure differential and detecting early formation of cracks by the change in pressure encountered. U.S. Pat. No. 3,667,862 discloses a method for detecting a crack in the wall of a hollow object by reducing pressure on the inside of the hollow body and sensing loss of vacuum formed. Other references showing detection of leaks in vessels by forming a sealed cavity over a possible leak location such as a joint or the like and then reducing pressure in the cavity to detect a leak by loss of the vacuum formed by tracer gas placed within the vessel or by soap bubbles are U.S. Pat. Nos. 3,949,596; 2,660,053; 1,371,484; 3,043,129; 3,524,342 and 4,002,055. However, these methods relate to detection of leaks in closed vessels, not the detection of crack formation in vessels in contact with fluid. These methods usually relate to the detection of pre-existing leaks and not the detection of cracks formed from environmental and wear conditions during a monitoring period which may extend over months or years. Those methods utilizing patches or enclosures and vacuum rely heavily upon the maintenance of vacuum or positive pressure in these lines, which lines are themselves subject to loss or crack formation such that the ambient atmosphere can enter these patches causing an alarm to sound. Further, such methods do not allow the particular location to be determined without extensive piping such that each patch is individually monitored.

U.S. Pat. No. 3,596,269 utilizes a number of resistance elements connected in parallel to indicate structural fatigue cracking and tearing in aircraft. Resistance elements are in parallel and apparently measure the degree of stress failure by determining the intensity of the resistance. U.S. Pat. No. 3,383,863 detects leaks in retaining pond linings by a grid of wires laid beneath the lining. When water or other fluid leaks from the pond through the lining an electrical circuit is completed between the separated intersecting connectors of the grid. The location of the leak is determined by measuring the resistance between crossing grid members, the leak being in the vicinity of the intersection of least resistance.

However, these methods are deficient since they require extensive piping in the case of vacuum or pressure monitor patches or pre-existing cracks in the case of the other references cited in order to be effective monitoring systems. It would be of great benefit to provide a method which can detect cracks in structural material, whether porous or non-porous, metallic or non-metallic, at an early stage of formation and locate the area of crack formation with specificity.

It is therefore an object of the instant invention to provide a process for early detection of cracks in structural materials subject to stress before the cracks traverse the materials. Other objects will become apparent to those skilled in this art as the description proceeds.

The instant invention provides a process and apparatus for the early detection of crack formation in structural materials subject to stress before the crack traverses the member, wherein the process comprises (a) affixing multiple liquid impermeable enclosures to the material to be monitored such that a crack forming in the monitored material will provide passage for liquid to enter the enclosures, either through the monitored material itself or by destroying the integrity of said liquid impermeable enclosures;

(b) sealing a resistor having a known value onto each of said enclosures, each of said resistors having one lead capable of liquid contact within the enclosure, said lead electrically isolated from the material being monitored and/or a second wire in the enclosure;

(c) forming a circuit connecting said multiple enclosures, wherein the opposite resistor lead in each enclosure is connected by insulated wire to means for measuring resistance and/or conductance, wherein each resistor alone or together with any combination of other resistors in said enclosures within the circuit provides a unique total resistance and/or conductance value when the exposed lead becomes liquid wet, and (d) monitoring the resistance and/or conductance of the circuit such that a crack in the monitored material will destroy the integrity of the enclosure, allowing liquid to enter the enclosure and complete the circuit, wherein the location of each fluid-filled enclosure will be determined by the resistance and/or conductance measured.

The process is applicable to both porous and non-porous structural materials.

DETAILED DESCRIPTION OF THE DRAWINGS

Figure 1:
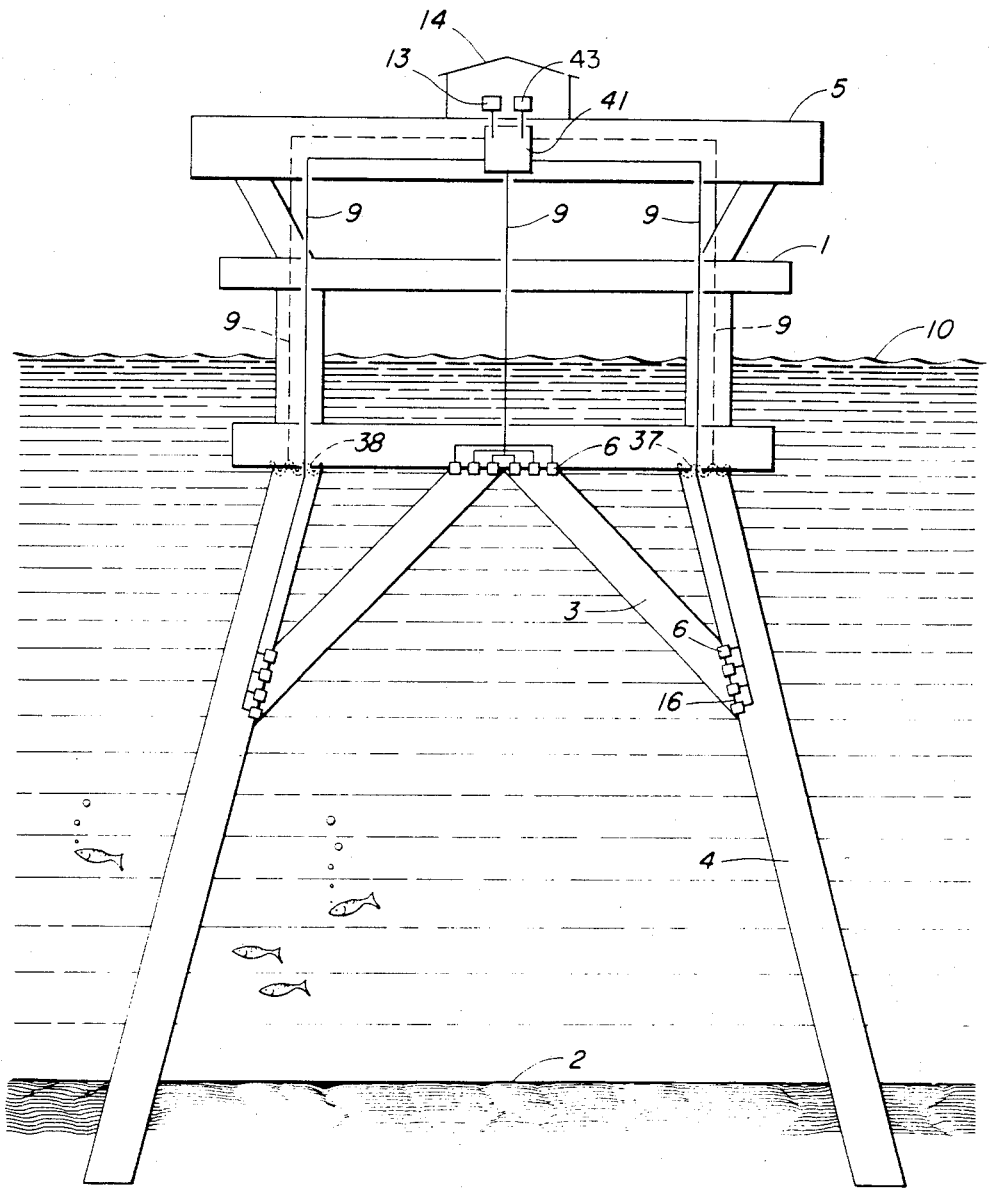
FIG. 1 is a schematic cross-section of an offshore platform having an example of the apparatus of the instant invention aboard for monitoring stressed members.

FIG. 1 illustrates a cross-section of an offshore platform having the apparatus of the present invention installed thereon.

The platform (1) rests upon and is fixed to sea floor (2) with its major portion submerged below the water level (10). It is comprised of various members including deck member (5), bracing member (3) and leg member (4). The members are joined together to form the platform by welds (16) as in the joint between member (3) and member (4). Patches of the present invention are connected by electrical line (9) to a monitoring apparatus (41). Exemplary serpentine configuration patches (37) and zigzag configuration patches (38) including similar patches not shown in other areas of the welds, these multiple patches of each type forming separate circuits were also employed to monitor the heat effected zone adjacent to weld joints joining other critical members stressed by wave action. Monitoring device (41) is connected to readout (13), which combination has the capability of monitoring patches in particular circuits and providing a leakage alarm when liquid enters any patch, such liquid detected by resistance or conductance change in the circuit associated therewith.

In addition the monitoring device (41) can be connected to a computer (43) which monitors all patches and indicates failure, optionally sounding an alarm. These components are sheltered by structure (14) on the platform. While FIG. 1 shows the monitoring device (41) receiving the signal from a single line (9) to a series of patches (6), it is recognized that the state of the art of multiplexing would allow the monitoring device (41) to be remote and close to the patches underwater, and from that location sends a readout signal by one cable as results are multiplexed from each line (9) leading to each patch (38), or group of patches (6) as in FIG. 8. Thus, the invention allows the readout from a series of circuits each of which contains multiple patches, to be connected to a multiplexer near the patches and remote from the readout device, all patches connected to the monitoring device by a single cable leading from the multiplexer.

Figure 2:
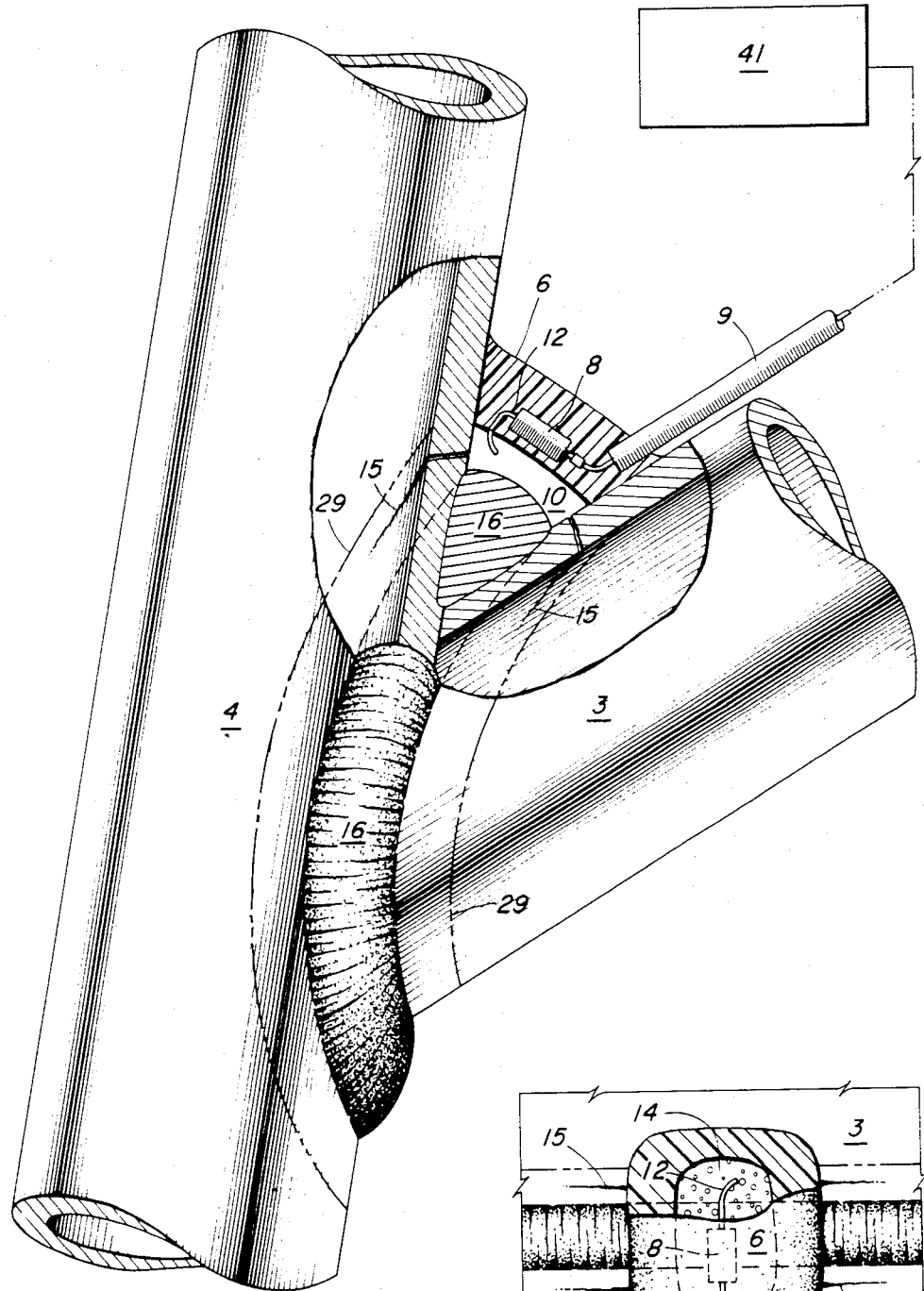
FIG. 2 illustrates a cross-sectional view of a patch sited to monitor the weld joint and associated heat effected zone (HAZ) where one member of the platform is joined to another member of the platform.

FIG. 2 illustrates a cross-section of bracing member (3) joined to upright member (4) by weld (16) having a heat effected zone (29) immediately adjacent on each side. Electrical line (9) is sealed within patch (6), line 9 connected directly to one lead of resistor (8) sealed within the material of patch (6) and having one bare lead (12) extending into the cavity void (10), the lead being electrically isolated from contact with the metallic structural member (3). Cracks (15) allow sea water outside the structure to enter the void and complete the electrical circuit between bare lead (12) and structure (3) and permitting monitoring device (11) to read a change in resistance in the circuit.

Figure 3:
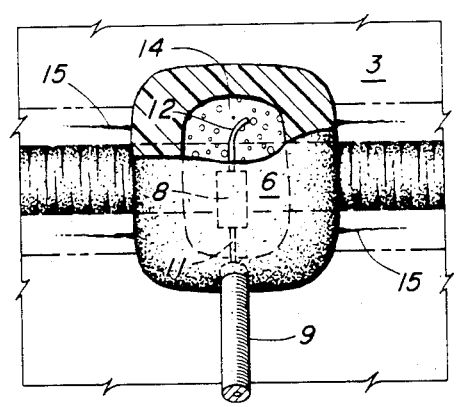
FIG. 3 illustrates a top sectional view of a patch situated on a weld and HAZ joining one member of the platform to another.

FIG. 3 illustrates a top sectional view of a patch similar to that shown in FIG. 2. Electrical line (9) directly contacts one lead (11) of a resistor (8) which is embedded within the material of the patch (6) such that fluid cannot contact the resistor itself. The opposite resistor lead (12) is in the void space of the patch, electrically isolated from the material of the structural member itself (3). Preferably, the bare lead (12) is electrically isolated by means of a liquid permeable nonconducting material (14) such as a sponge or the like. Integrity of the patch is violated by cracks (15) which allow liquid to enter the patch and complete the electrical circuit.

Figure 4:
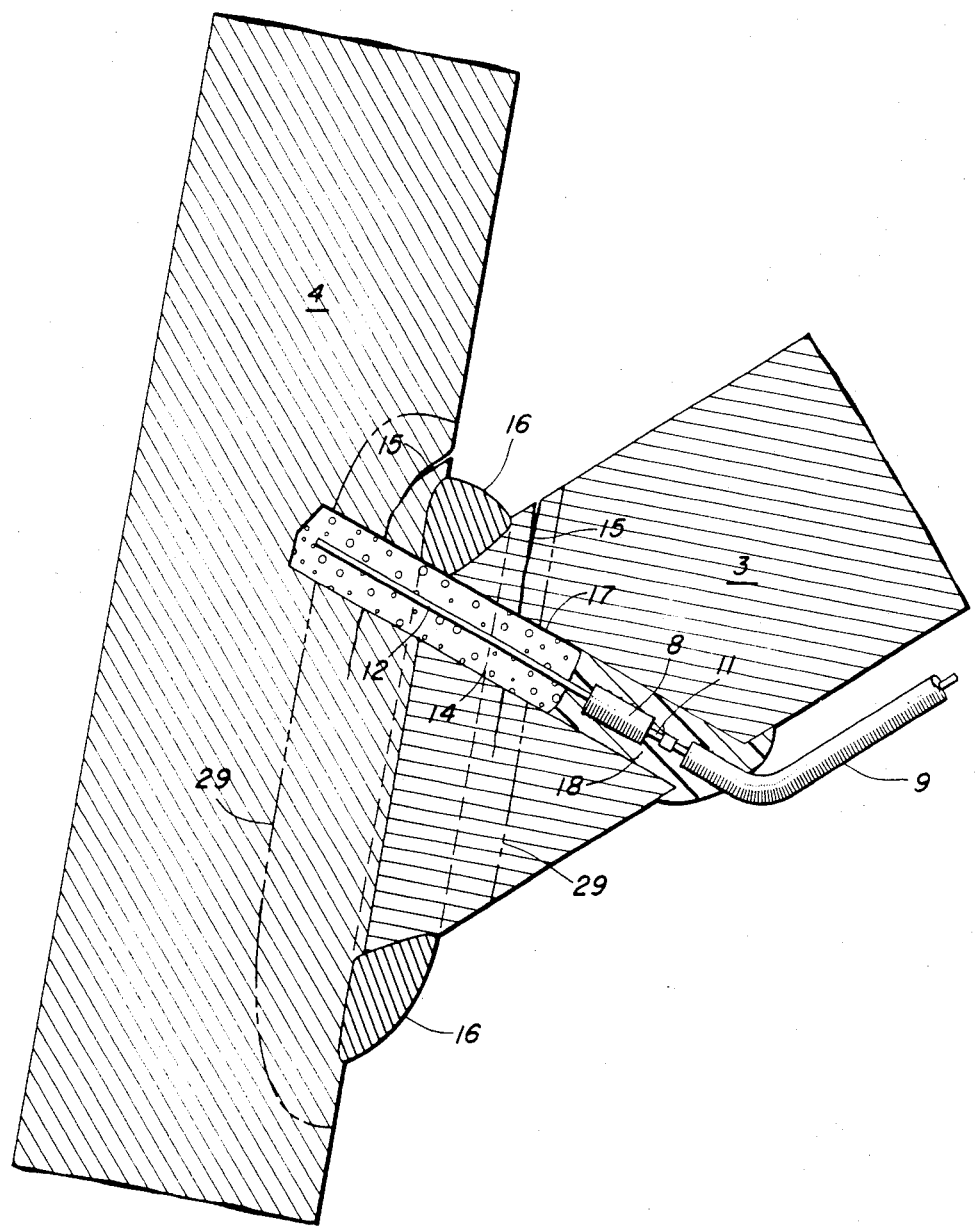
FIG. 4 shows a cross-sectional view of an embodiment wherein a cavity is formed into the heat effected zone near a weld joint on a platform.

FIG. 4 illustrates another embodiment by a cross-sectional view. Electrical line (9) connects to one lead (11) of resistor (8) which has bare lead (12) inserted into the cavity and held in electrical isolation from structure (3) by liquid permeable non-electrical conducting material (14). This cavity penetrates a portion of the heat effected zone (29) adjacent to weld (16) subject to cracks (15) which allow liquid to enter the cavity (17) sealed by liquid impermeable sealant (18) to complete the electrical circuit provided by wire (9) and structure (3) and allowing a resistance or conductance to be read by the monitoring device (not shown). Any cracks (15) penetrating the heat effected zone (29) to the cavity (17) result in entrance of liquid from the environment, which immediately completes the circuit and provides a change in resistance or conductance in the circuit to be monitored, which change triggers an alarm, not shown in FIG. 1.

Figure 5:
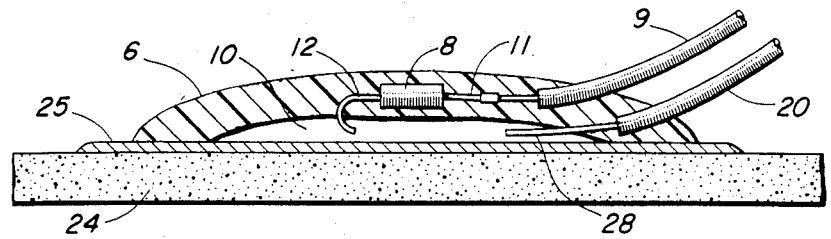
FIG. 5 shows a cross-sectional view of an embodiment of the invention wherein the patch contains a resistor, an exposed lead and an insulated second wire monitoring porous material.

FIG. 5 illustrates yet another embodiment by vertical cross-sectional view. Electrical line (9) is connected within the body of the patch to one end (11) of a resistor (8) which is sealed within the patch having a lead wire (12) free of the patch material but in electrical isolation from the structural material (3). A second insulated wire (20) penetrates the patch (6) with a bare lead (28) exposed within the patch cavity. Material (24) is porous material, wherein the patch is bonded to such material by a frangible liquid-impermeable material (25). Cracks in the porous material will cause fractures in the frangible liquid-impermeable material (25) such that liquid will enter the cavity and complete the circuit, the particular cavity being breached determinable by the amount of resistance and/or conductance.

Figure 6:
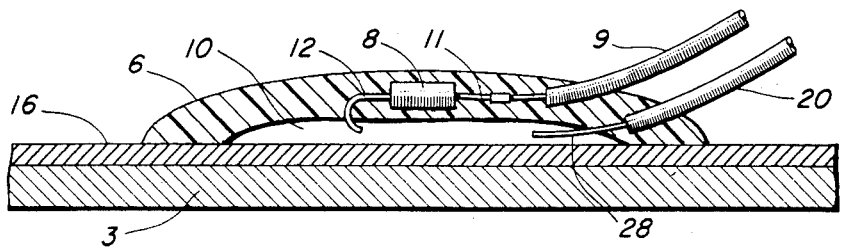
FIG. 6 illustrates a cross-sectional view of an embodiment of the invention wherein a patch comprises a resistor overlaying a metallic material which forms the electrical circuit return or the circuit can be completed by an optional return wire (20).

FIG. 6 illustrates another cross-sectional view of an embodiment wherein insulated wires (9) and (20) are sealed into cavity (6), wherein insulated wire (9) is connected through encased lead (11) to resistor (8) having a bare wire (12) extending into cavity area (10), wherein bare leads (28) and (12) are electrically insulated from both the weld (16) and metallic structural member (3). In this embodiment, the return is provided by wire (20), and although no liquid impermeable electrically insulated material is shown between lead (28) and lead (12), such material can optionally be used.

Figure 7:
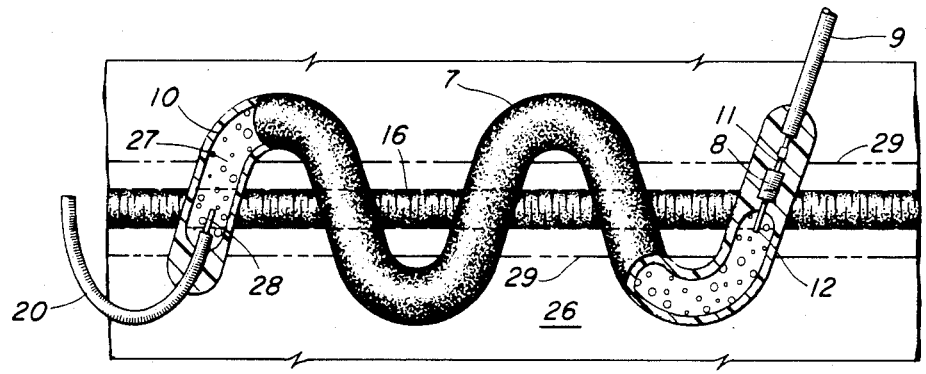
FIG. 7 illustrates a patch embodiment having a serpentine configuration monitoring a weld joint and the heat effected zone associated therewith.

FIG. 7 illustrates an embodiment wherein the patch (7) has a serpentine configuration. Electrical line (9) is sealed into patch (7) and connected to resistor lead (11), and to resistor (8) which has an electrical lead (12) in the cavity void together with return wire (20) which has bare lead (28) affixed some distance from bare lead (12). The cavity contains a liquid permeable material (27) having impregnated therein a dry electrolytic salt which provides electrical contact once liquid contacts the salt and places it in an ionized condition. The serpentine configuration patch crisscrosses weld (16) and heat effected zone (29) on substrate (26).

Figure 8:
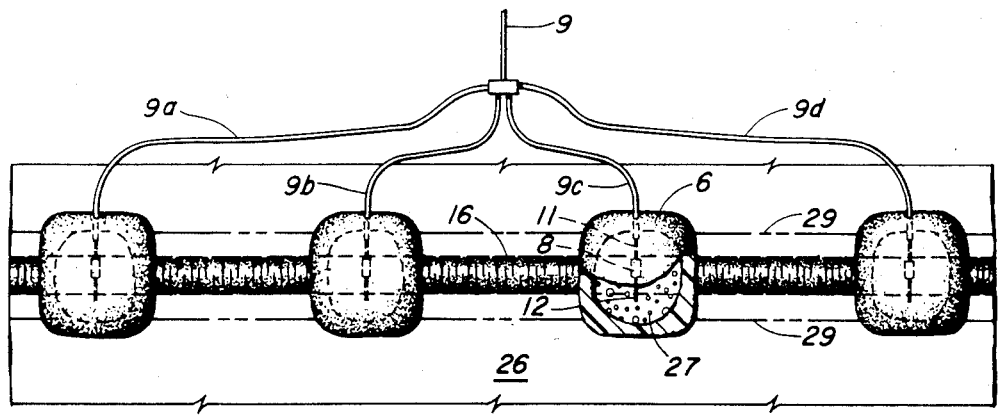
FIG. 8 illustrates an embodiment wherein a series of patches are employed to monitor a weld joint and a heat effected zone, with the electrical connections illustrated. In such an embodiment using a metallic structural member no return wire is necessary.

FIG. 8 illustrates by top view section the instant invention wherein a plurality of patches are employed to monitor a weld (16) and heat effected zone (29) on substrate (26). Patches comprising impermeable material (26) having therein cavities situated over the heat effected zone (29) and weld (16) are sealed from the environment. Insulated wire (9) is joined to insulated electrical lines (9a), (9b) (9c) and (9d), each connecting to one end (11) of a resistor (8) in each patch. A resistor (8) is placed in each patch, each resistor having a different value, such that the resistance and/or conductance of any combination of resistors has a unique value. The patch contains a liquid permeable material (27) which electrically insulates bare lead (12) from weld (16) and substrate (26). In the embodiment pictured, substrate (26) provides a signal return.

Thus the present invention provides a simple electical means of detecting a crack-caused leak into a sub-liquid cavity on or in a structure in identifying a cavity by means of a sealed resistor in the cavity. The resistor has one lead with a bare end projecting into the cavity which is electrically isolated, preferably with a liquid-permeable barrier from the structure. Alternately, a second wire having a bare lead will be in the cavity. If the structure is a non-electrically conducting material or a porous material, a second return wire is necessary. These bare leads are electrically isolated, preferably with a water-permeable electrically non-conducting material.

The opposite end of the resistor is connected by insulated wire to a resistance or conductance measurement device. While resistance can be measured directly, normally it will be preferred to measure conductance (the reciprocal of resistance) because of the linear readout obtained.

Representative but non-exhaustive examples of suitable measuring instruments are the Fluke 8060A multimeter (Trademark of and sold by Fluke Instrument Co.) with a $2\mu$ siemens range, and Fluke 8520A $5\frac{1}{2}$ digit Digital multimeter with IEEE-488 interface to a computer with a 200 nono-siemens range and resistance ranges from 10 ohms to 10 megohms.

Several different crack detecting cavities are monitored on the same insulated wire and measurement device by using different values of resistors for each cavity. Each resistor has a different value and in any combination provide a unique value such that any cavity intercepted by a crack in the material is identified by resistance or conductance when the resistor is shorted to the structure or the alternate second wire. Additional later cracks intercepting other patches in the circuit provide further change in resistance or conductance. The leads which form the parallel circuit from the resistors can be found at a location near the multiple patches, necessitating only a single wire to the multiplexing or monitoring device. Thus the multiple cable or conduit of the prior art are avoided.

Thus cracks propagating through this material which intercept with a patch provide a leak path from the exterior to the interior of the patch, this leak then readily detected by the electrical resistance or conductance of that particular patch.

If the insulated lead developes a fault in the insulation below liquid level, when the monitored material is used as a signal return, then a resistance reading below the value of any combination of resistances results, indicating a malfunction of the system. However, when an alternate insulated wire is used as a signal return, the insulation in both the signal wire and the return wire must fail to cause a malfunction. In normal operation, a no crack-no fault reading is very high resistance. Any separation or failure of the wire below liquid level results in a fault. Continuity checks are easily made on any wires above liquid level by a simple visual observation.

Thus the present invention depends upon the multiplicity of patches of desired configurations, each having sealed therein a resistor, such that the combination of resistors provide unique values for any patch or combination of patches which provides an electrical circuit which results in resistance and/or conductance. When ambient liquid penetrates into the patch, the resistor provides an electrical signal indicating resistance or conductance in the line. This signal can be used to trigger an alarm such as a light or bell. The circuits can be monitored continuously or intermittantly by either manual or computerized systems, such that a change in signal will immediately indicate the patch or patches which have been breached to permit liquid to enter.

The present invention is useful in any system wherein liquid contacts the structural member. The liquid can be on the interior of the structural member, such as in ships carrying liquids, railcars and the like, or on the exterior of a member such as on on offshore platform or the like.

The instant invention is likewise useful with liquids which are not normally considered electrolytes, by the simple expedient of providing a dry salt in the interior of the patches, such that liquid entering the patch provides an electrolyte material which will conduct electrical current and trigger the alarm.

The instant invention is useful with both permeable and non-permeable structural materials, although it will be used most commonly on impermeable materials.

When utilizing the instant invention on porous materials, a frangible, liquid impermeable seal is placed on the porous material as described in U.S. Pat. No. 4,135,386. Thereafter, the resistors are embedded in the patch with a bare lead showing, such that any crack in the porous material provides access for liquid to complete the circuit.

The sealant employed for making patches according to the present invention can be any of a number of materials. For example, solder, brazing materials, epoxy based sealants, silicone materials, butyl rubber sealants, hot melt formulations or any of a variety of other materials can be employed if desired.

In a preferred embodiment, a very suitable and versatile material found to be useful in the present invention is Knedatite sealant, (trademark of and sold by Knedatite division of Polymeric Systems, Inc., Pottstown, Pa.). This material is an epoxy/polyamide system supplied as a 2-part hand mixable tape which is kneaded together and cures within a few hours. This epoxy-based sealant is usually formed into patches which contain the resistor with exposed end and cures within a short time after mixing into a flexible, tough, hard, liquid impermeable material.

This material can also be utilized for adhering frangible bases of the patch to porous material. Frangible material such as glass tubes or metal foil at the base of an epoxy-type patch will provide an easily broken system to allow liquid to enter if porous material is cracked. However, this epoxy resin will likewise crack under stress and provides an adequate sealant material when applied directly onto the porous substrate being monitored. Other useful materials are epoxy adhesives and rigid thermoplastic adhesives. When applied to porous materials, adhesives should be selected which have a strength equal to or less than the permeable material being monitored.

Whether the electrical circuit is completed through the structure being monitored, or using a return wire, the leads must be electrically insulated from one another. In the preferred embodiment of the present invention this is accomplished by utilizing a liquid permeable, electrically non-conducting material such as a sponge or synthetic foam. Any of a number of other materials can likewise be utilized so long as the criteria of liquid impermeability and electrical insulation when dry is met.

The present invention, while used in a preferred embodiment in an electrolytic environment such as sea water, is likewise useful in environments where the liquid contacting the monitored material is not normally considered an electrolyte. Such liquids include fresh water and the like which do not readily conduct electrical current. However, these liquids can be transformed into electrolytes by utilizing a dry, low conductance hygroscopic or deliquescence material in the dry cavity, or dispersed in the insulating material, such that when moist air or a liquid enters the cavity through a crack the material will become wet and will act as a conductor (or electrolyte). Examples of such materials are common table salt, sodium hydroxide, potassium hydroxide, sodium dichromate, sodium cyanide, sodium permanganate, potassium triiodide, potassium ortho phosphate and potassium thiosulfate. Since the patch will be replaced once ruptured and the crack repaired, it is not necessary that these materials be non-destructive to the resistors or the like. The only criteria is that these materials form electrolytes when contacted by a liquid.

Suitable materials to act as water permeable insulating materials include paper, cloth prepared of natural or synthetic fibers, open cell foam plastics and the like. A fabric woven of synthetic fibers is quite suitable. Electrical conductors such as wire must of course be excluded.

It is necessary that the portion of the member being monitored not be entirely sealed from the liquid contacting structure. When this happens, cracks can propagate under the sealant and become quite extensive before a cavity is breached. Usually coverages of 10% or less of the structure being monitored are quite adequate, especially when serpentine configurations and the like are utilized.

Although the patches of the present invention have been described as squares, retangles, or serpentine configurations, it is readily apparent that any configuration necessary can be utilized. For example, holes can be drilled into the structure being monitored and the resistor sealed therein. Other shapes such as starbursts or circles or any irregular shape can be utilized as necessary.

Thus the present invention also provides an apparatus for monitoring formation of cracks and materials in contact with fluid, which apparatus comprises:

(a) multiple fluid impermeable enclosures attached to said monitored material, (b) resistors sealed into each of said multiple enclosures, each resistor having a known value wherein such resistor, whether measured alone or together with any combination of resistors provides a unique total resistance and/or conductance value, each of said resistors having one lead capable of electrical fluid contact, each of said leads electrically isolated by a fluid permeable barrier from the monitored material and/or a second wire in the enclosure, such that fluid entering the enclosure completes a circuit and provides a measurable resistance and conductance in said circuit, and (c) means for monitoring the resistance and/or conductance of the circuit so formed, such that resistors in contact with fluid provide resistance in the circuit.

The instant invention is more concretely described with reference to the example below. The example is provided to illustrate the present invention and not to limit it.

EXAMPLE

The structural member is monitored using the patch configuration described in FIG. 8 and utilizing in each patch a resistor in parallel with other resistors. The four resistors will have values of 1, 2, 4 and 8 megohms. The value of the resistors in parallel is described as R=total resistance while (1/R)=siemen conductance, such that the value of the total circuit is $(1/R)=(1/R_1)+(1/R_2)+(1/R_3)+(1/R_4)$. This configuration is utilized to monitor a structure as described in FIG. 8 and as set forth in Table 1. In the table, X designates patches with leaks, O designates patches without leaks.

TABLE 1

DETECTOR PATCH IN PARALLEL

| $\frac{1}{R}$ Conductance Siemens | No. 1 1 meg | No. 2 2 meg | No. 3 4 meg | No. 4 8 meg | R Meg ohms Total. Resistance |
|---|---|---|---|---|---|
| 0.125 | O | O | O | X | 8 |
| 0.250 | O | O | X | O | 4 |
| 0.375 | O | O | X | X | 2.66 |
| 0.500 | O | X | O | O | 2 |
| 0.625 | O | X | O | X | 1.66 |
| 0.750 | O | X | X | O | 1.33 |
| 0.875 | O | X | X | X | 1.14 |
| 1.000 | X | O | O | O | 1. |
| 1.125 | X | O | O | X | 0.89 |
| 1.250 | X | O | X | O | 0.80 |
| 1.375 | X | O | X | X | 0.73 |
| 1.300 | X | X | O | O | 0.66 |
| 1.625 | X | X | O | X | 0.62 |
| 1.750 | X | X | X | O | 0.57 |
| 1.875 | X | X | X | X | 0.53 |
| .000 | O | O | O | O | ∞ |

As can be seen from the table, the value of the circuit can be measured either directly in Meg ohms as total resistance or the inverse of resistance (conductance). In general, it would be preferred to read the circuit as conductance, since this is a straight line function and provides a ready indication to the particular patch or patches which have been breached.

In a preferred embodiment this circuit or circuits will be monitored by a computer system such that any breach of a particular circuit will immediately provide the location of the breached area or areas.

Although the system has been illustrated as containing only four patches, there is theoretically no limit to the number of patches that can be monitored on a single circuit. The resistance of the patches is selected based on the hexadecyl systems, such that the next (or fifth) patch would have a resistor with 16 meg ohms, the sixth with 32 meg ohms, the seventh with 64 meg ohms, and so forth. For practical purposes and for ease of calculation, normally only about 8 or less patches would be used in any one circuit, though this is strictly based on end use of the particular monitoring system.

While certain embodiments and details have been shown for the purpose of illustrating this invention, it will be apparent to those skilled in this art that various changes and modifications may be made herein without departing from the spirit or scope of the invention.

We claim:

1. A method for monitoring crack formation in materials in contact with liquids comprising
   (A) affixing multiple liquid impermeable enclosures to the material to be monitored such that a crack forming in the monitored material will provide passage for liquid to enter the enclosures either through the monitored materials or by destroying the integrity of said liquid impermeable enclosures;
   (b) sealing a resistor having a known value onto each of the enclosures, each of the resistors having one lead capable of liquid contact within the enclosure, said lead electrically isolated from the material being monitored and/or a second wire in the enclosures;
   (c) forming a circuit connecting the multiple enclosures wherein opposite resistor leads from each enclosure are connected by insulated wire to means for measuring resistance and/or conductance wherein each resistor alone or together with any combination of other resistors in said enclosures within the circuit provides a unique total resistance and/or conductance value if the exposed lead becomes liquid wet, and
   (d) monitoring resistance and/or conductance of the circuit, such that a crack in a monitored material will destroy the integrity of the enclosure, allowing the liquid to enter the enclosure and complete the circuit, wherein the location of each fluid filled enclosure is determined by the resistance and/or conductance measured.

2. A method as described in claim 1 wherein the exposed resistor lead is electrically insulated from the monitored material by a liquid permeable barrier.

3. A method as described in claim 2 wherein the enclosures contain a second wire electrically isolated by a fluid permeable barrier from the resistor lead capable of electrical liquid contact, and wherein fluid entering said enclosure will complete an electrical circuit through the resistor.

4. A method as described in claim 3 wherein the means for detecting resistance activates an alarm system upon change in the resistance of the circuit.

5. A method as described in claim 4 wherein multiple circuits are joined to a multiplexer and a single cable connects to a monitoring device.

6. A method as described in claim 5 wherein the circuit is monitored at intervals by a computer capable of determining the total resistance and/or conductance of the circuit, thereby locating specific enclosures which contain liquid.

7. A method as described in claim 6 wherein the isolated electrical resistor lead capable of electrical liquid contact is surrounded by a dry material capable of forming an electrolyte when in contact with a fluid.

8. A method as described in claim 7 when located on an offshore platform.

9. A method as described in claim 8 wherein the fluid impermeable closures are formed of epoxy resin.

10. An apparatus for monitoring formation of cracks in materials in contact with fluids, comprising
    (a) multiple fluid impermeable enclosures attached to said monitored material,
    (b) resistors sealed into each of said multiple enclosures, each resistor having a known value wherein such resistor, whether measured alone or together with any combination of resistors provides a unique total resistance and conductance value, each of said resistors having one lead capable of electrical fluid contact, each of said leads electrically isolated by a fluid permeable barrier from the monitored material and/or a second wire in the enclosure, such that fluid entering the enclosure completes a circuit and provides a measurable resistance and conductance in said circuit, and (c) means for monitoring the resistance and/or conductanc of the circuit so formed, such that resistors in contact with fluid provide resistance in the circuit.

11. An apparatus as described in claim 10 wherein the enclosures comprise epoxy resin, metal foil and plastic film.

12. An apparatus as described in claim 11 wherein multiple circuits each containing multiple patents are connected to a multiplexing device, and from said multiplexing device to a monitoring device by a single cable.

* * * * *